(12) United States Patent  
Hirata

(10) Patent No.: US 9,776,015 B2
(45) Date of Patent: Oct. 3, 2017

(54) TEXTILE PRODUCT

(71) Applicant: Mario Hirata, São Paulo (BR)

(72) Inventor: Mario Hirata, São Paulo (BR)

( * ) Notice: Subject to any disclaimer, the term of this patent is extended or adjusted under 35 U.S.C. 154(b) by 426 days.

(21) Appl. No.: 14/604,064

(22) Filed: Jan. 23, 2015

(65) Prior Publication Data

US 2015/0224230 A1 Aug. 13, 2015

Related U.S. Application Data

(62) Division of application No. 12/935,491, filed as application No. PCT/BR2009/000087 on Apr. 3, 2009, now Pat. No. 8,968,819.

(30) Foreign Application Priority Data

Apr. 7, 2008 (BR) ..................................... 0801857

(51) Int. Cl.
*A61N 2/00* (2006.01)
*A61N 5/06* (2006.01)

(52) U.S. Cl.
CPC .... *A61N 5/0613* (2013.01); *A61N 2005/0645* (2013.01); *A61N 2005/0659* (2013.01)

(58) Field of Classification Search
CPC .......... A61N 5/0625; A61N 2005/0645; A61N 2005/0659
See application file for complete search history.

(56) References Cited

U.S. PATENT DOCUMENTS

| | | | |
|---|---|---|---|
| 6,652,446 B1 * | 11/2003 | Bove ........................ | A61N 2/06 600/15 |
| 6,666,813 B1 * | 12/2003 | Ardizzone ............... | A61N 2/06 219/211 |
| 6,939,287 B1 * | 9/2005 | Ardizzone ............... | A61N 2/06 600/15 |
| 8,968,819 B2 * | 3/2015 | Hirata .................... | A61K 8/027 427/2.31 |
| 2002/0077523 A1 * | 6/2002 | Ardizzone ............... | A61N 2/06 600/9 |
| 2014/0209594 A1 * | 7/2014 | Besner ..................... | A61N 5/06 219/217 |

FOREIGN PATENT DOCUMENTS

JP 2002038370 A * 2/2002

* cited by examiner

*Primary Examiner* — Kaitlyn Smith
(74) *Attorney, Agent, or Firm* — B. Aaron Schulman, Esq.; Stites & Harbison PLLC

(57) ABSTRACT

Improvements applied to a textile product, and more particularly wherein the improved product is a woven textile product—fabric containing bioceramic microparticles embedded into the fibers thereof with high capacity of irradiation in the infrared region, provided to be used both in humans and animals, more particularly the invention is related to a textile product containing bioceramic microparticles with high capacity of infrared irradiation which, in contact with the heat of the human body, is capable of transmitting infrared radiation in the range between 3 μm and 14.8 μm, preferentially in the 14.8 micron range, said infrared radiation at this wavelength being capable of regulating the blood microcirculation, as the result of its high protection, the blood microcirculation being the nervous center of human and/or animal metabolism.

17 Claims, 5 Drawing Sheets

TEXTILE PRODUCT

CROSS REFERENCE TO RELATED APPLICATIONS

This application is a divisional of U.S. application Ser. No. 12/935,491, having a filing date of Dec. 22, 2010, which is a 371 application of PCT/BR2009/000087, filed Apr. 3, 2009, said applications incorporated herein by reference.

TECHNICAL FIELD

The present invention is directed to improvements applied to a textile product, particularly a textile product containing bioceramic microparticles imbedded into the fibers thereof with a high irradiation capacity in the infrared range, provided to be used both in humans and animals, and more particularly the invention is related to a textile product containing bioceramic microparticles with high capacity of infrared irradiation which, in contact with the heat of the human body is capable of transmitting infrared radiation in the range between 3 µm and 14.8 µm=(microns), preferentially in the 14.8 micron range, whose infrared radiation, at this wavelength, is capable of regulating the blood microcirculation as a result of its high protection action, the blood microcirculation being the nervous center of human and/or animal metabolism.

STATE OF THE ART

It is of common knowledge that diseases such as sleep disorders, fatigue, stress and psychiatric disorders, among others, have been intensified presently, causing pains and discomfort, thus impairing the life quality of human beings.

One of the causes of such problems is the deficiency in the blood circulation, the result of which is a number of disorders in the human metabolism, thus degenerating several functions of different organs and in many cases fully or almost fully destroying the organs.

A bad blood circulation is caused by different factors, such as hormonal disorders, heredity, poor feeding, sedentary behavior, smoking and use of alcoholic drinks, exaggerated consumption of salt or sugar, use of drugs, among other factors.

One of the most traditional cases is related to varix, whose degeneration is caused by the relevant bad blood circulation that makes the walls of the veins less elastic, weakening the legs so that that get swollen, painful, tired and heavy.

Traditional medical or therapeutic treatments have been used to reduce or prevent bad circulation problems, among them, the constant use of medications, the practice of physical exercises, the practice of lymphatic draining techniques, the use of creams especially developed for that end, among others.

On the other hand, cellulite, for example, is caused by a severely bad blood circulation, causing an alteration in the skin fabric located between the dermis and the hypodermis, a bad blood circulation that can be caused by organic disorders, hormonal alteration, heredity, poor feeding, drinking, smoking, excessive consumption of salt or sugar, among other factors.

Several traditional treatments have been used to fight bad blood circulation, including the use of medicines, physical exercises, food re-education, massage treatments, among others.

Techniques that are used for different therapies are also known, for example, short, medium or long range/range infrared, but until now there has been no notice of efficiently proven methods for the treatment of bad blood circulation that may reach the microcirculation ultimately.

The infrared is a region or range/range of the electromagnetic spectrum located between the regions of visible light and microwaves. The infrared radiation is an electromagnetic radiation with long wavelengths, thus being located in the invisible portion of the electromagnetic spectrum, wherein the photons of infrared light are less powerful than the photons that compose the visible light and, therefore, the infrared radiation s imperceptible to the human eye, since the infrared radiation is too excessive to be perceived visually but can be perceived only by means of heat. The waves of the infrared range have a length varying between 0.76 and 1,000 µm—microns. These electromagnetic waves (or radiation) are generated on the grounds that all the sunrays are electromagnetic radiations and each of them is provided with its own characteristics, in accordance with the wavelengths and frequencies thereof.

A brief research of patents carried out in the relevant agency—INPI—reveals the concern related to the search for developing methods, processes, techniques and products that can use infrared radiation for different therapies.

Thus, particularly regarding the use of the long infrared radiation, we have found document PI 0502394-7, that is directed to a comforter comprised of two textile parts, 100% cotton, percale plus with 200 threads, the function of which is to coat the top and bottom parts of the comforter, a 160 g/m² polyester resin filling that coats the inner layer composed of long infrared irradiating catalyzing biofiber like a sandwich, the purpose of said product being to catalyze the long waves of the infrared rays existing in our environment, such rays emanating from any source of energy, either light or heat, transforming the frequency of its waves having several and differentiated longitudes into frequencies that vary between 4~14 microns of distance between the crests of its waves, such frequencies being the ones that make the water molecules in the body vibrate. When the human body at its normal average temperature of 36 degrees centigrade radiates long infrared rays, at a frequency of 9~10 microns, the biofiber that composes the filling of the comforter catalyzes such waves by speeding up same and sending them back to the human body, thus making the water molecules of the body to vibrate at a higher intensity, dissolving the clusters of water in the body, setting the toxins that were expelled in the osmosis free, thus being eliminated more easily through the natural ways of the body itself, improving the biological quality of the water that contains living organisms, facilitating the cellular absorption, no matter if they are animals or vegetables.

In the sequence of the research, patent MU 8600905-2 was identified, which patent is directed to the protection of a constructive configuration applied to a magnetic orthopedic cushion by using long infrared radiation, characterized by being comprised of a parallelepiped-shaped foam body, involved in a fully anti-allergic fabric, one face of said parallelepiped-shaped body being provided with handles having with Velcro straps for an adjustable closing when said cushion is placed on one of the legs of the patient, said cushion being internally provided with a plurality of ferrite bodies and waffles located inside the parallelepiped-shaped foam body, covered with a thin foam layer and ultimately externally coated with the anti-allergic fabric. Another proposal, as foreseen in the body of the specification, is to solve vertebral problems, pains in the body and blood impurities while the patient is sleeping, thus obtaining a product integrated with real possibilities of a cost-effective industrialization, minimizing costs, with better results and high safety standards; besides providing a constructive configuration in a magnetic orthopedic cushion with long infrared radiation that solves vertebral problems, pains in the body, blood impurities of a patient while he/she sleeps, so that said cushion is trapped in one leg of the patient by means of safe comfortable adjustable straps, provided with Velcro.

A third document was found under number PI 0504066-3 dated 9 Jun. 2005, the proposal of which is the recompilation of experimental medical-scientific studies characterized in that the studies and tests in laboratories have proven the medical-scientific application of the use of the waffles and bio-ceramic powder, both containing (civlf) in the confection of apparel in general, as well as its application to footwear and mattresses, its function being carried out both at the cellular level and in the peripheral regions of the blood circulation, thus demonstrating the vast and wide application thereof for the health and the welfare in a general way. It was scientifically proved that its use in the long run can not only prevent a myriad of malignances, but also help in the treatment of those already installed in a sick human body that needs something to reinforce the direct treatment, from a number of disease so common to humanity presently.

In this object, through its technical report, it is disclosed that by taking into account the need of a biological feedback that can assure the continuous functioning of the system, it can be assumed and speculated that the IR radiation emitted by the living fabric can conduct a sort of information that would interact with its generating mechanism. For example, an effort of the IR radiation emission in a zone can reflect to the biological membranes, thus diminishing or potentiating the power converting processes related thereto, in such a way that the biological production is reduced or increased, and such possibility of transmitting fast intercellular communications that allow for the energy change, added to the ability to access the resonance frequency (long infrared radiation) with large size molecules and clusters of water, can be in the change of the intensification of the biochemical reactions and the therapeutic potential that clinical studies reveal. With regard to the waffle, bioceramic powder and fiber (CIVLF), they are catalyzing material having wavelengths of 4-14 $\mu$m, the CIVLF being a white material having a 15 mm diameter when in the form of a waffle, in a light gray color when it is a powder without fragments, and while in the form of fibers it has a mixture of thermoplastic bioceramic resin in its composition, where a colloidal mixture is incrusted, the basic material used being Sil-Mg—Al-Mm-Na—Fe, a) some of the most important physical characteristics are the following ones: it is capable to emit selectively a IR electromagnetic wave having a length between 4 and 14 $\mu$m, b) the CIVLF is capable to emit more energy as it increases its temperature, but the spectral distribution of the energy in LANGLEYS, the amount of radiating energy of a certain wavelength, emitted by a body per area and time unit is called monochromatic emittance and the total amount of radiating energy of all the wavelengths that are emitted by a body per area and time unit is called emittance, according to Planck law, the monochromatic emission depends not only on the wave but also on the absolute temperature the body is at. The CIVLF has a high index of temperature absorption, taking about 15 seconds to reach 40° C., while the other products take approximately 27 seconds to reach the same temperature.

The documents referred to in the present specification disclose the use of long infrared radiation, however without evidence by clinical research, despite the citations found in PI 0504066-3. They are not within the actual needed infrared irradiation ranges for the therapeutic functions proposed, besides not encompassing specifically the process of regulating the blood microcirculation that, only as a consequence of the action on the microcirculation, will regulate said circulation, for the purpose of stabilizing both of them, thus reducing considerably the health problems already diagnosed or to be dealt with in the future. Also, the infrared radiation transmitted by this product resulting from all research carried out and proven by the applicant reaches the 14.8 micron range, a value not disclosed previously, said percentage being consequently capable of a fierce protection and as a result acting with better quality and getting new actual results.

BRIEF DESCRIPTION OF THE OBJECT

In view of the already disclosed object concerning the infrared in the medium to long range, all distinct from the present invention, the applicant, being aware of the processes above identified and operating in the segment of therapeutic treatments, besides being a researcher in the human health area, developed the present invention that is particularly directed to an improvement applied to a textile product, particularly containing incorporated bioceramic microparticles imbedded into the fibers thereof with high capacity of irradiation in the infrared region, provided to be used in human beings and animals. The present invention is specifically directed to a textile product containing bioceramic microparticles with high capacity of infrared irradiation that in contact with the heat of the human body is capable to transmit infrared radiation in the 3 $\mu$m to 14.8 $\mu$m=microns range, preferentially with the 14.8 microns range, whose infrared radiation at this wavelength is capable of regulating the blood microcirculation, as a result of its high protection, the blood microcirculation being the nervous center of human and/or animal metabolism.

The electromagnetic radiation is emitted from any body or substance that is at a temperature other than absolute zero, that is, −273.15° C. (degrees centigrade) or −459.67° F. (Fahrenheit degrees), whose radiation emission range depends on the temperature of the substance, while the intensity emitted at each wavelength is varied as a result of the chemical composition of the substance which regulates the absorptions and emissions of the electromagnetic radiation typical of atoms and molecules that constitute physical substances. On the other hand, at a certain temperature, at each wavelength there is an upper limit for the radiation of the matter/bodies, such limit being that attained by an ideal body known as black body. As a reference, at a temperature of 37° C. the maximum radiation emitted by any substance is that of the black body at 37° C., and therefore any substance at 37° C. emits its radiation concentrated in the infrared spectrum, between 3 $\mu$m and 25 $\mu$m.

A black body is a solid body whose radiation emission properties do not depend on the material, but only on its temperature. To satisfy this physical property the need to keep the black body at a constant temperature implies that the black body needs an energy balance in which all the radiation absorbed also is emitted irrespective of the spectrum range, what is equivalent to say that its total emissivity equals the unit Ecn=1. For the bodies in general, this energy balance (absorption/emission) may not be reached in any spectrum range (as in the black body) and, therefore, generally its full emissivity is lower than one. Thus, the emissivity of any body is the measure of its capacity of emitting radiation at a given temperature, in comparison with the maximum possible emission, that is, in comparison with the possible emission, that is, in comparison with the emission of the black body. This comparison can be made at any wavelength range (spectrum range). Technically, the comparison is made by virtue of the radiance of the body in relation to the radiance of the black body, both at the same temperature and for the same spectrum range, thus being a number between zero and one, physically valid under such specific conditions. Therefore, it can be concluded that a body can have a high emissivity in a spectrum range and a low emissivity in another one.

For the product being developed, the total directional emissivity, at a human body temperature of 37° C. and at an room temperature of 25° C., the infrared spectrum range was determined between 3 μm and 14.8 μm preferentially applied in the 14.8 range to attain the results proposed herein, in the direction normal to the surface, that is, the total normal emissivity of the fabric under such specific conditions.

Thus, significant differences between this object are reached and the one disclosed in the patents previously cited, particularly in reason of PI 0502394-7 and PI 0504066-3, since the first one allocates the maximum range of 14 microns-1.tm, and the second one being limited to the wavelengths in the order of 4-14 g, not attaining any novelty since technical information already known and disclosed previously including the patents mentioned herein are shown in the respective report, besides the fact that they do not encompass the specific technical field of blood microcirculation, so that some citations had reached only the circulation at most but not the microcirculation. More precisely, the fabric proposed herein contains bioceramic microparticles in the order of up to mesh 1,350, thus not modifying the elasticity and characteristics of the fabric, with high capacity of infrared irradiation which, in contact with the heat of the human body, transmits waves in the medium to long range/ band, thus balancing and stabilizing the blood microcirculation, for the purpose of reducing the physical problems and consequently the several diseases that have resulted in the death in view of this disorder.

In another version, it is foreseen that the infrared radiation obtained herein radiates waves in the 3 μm to 14.8 preferential in the range of 14.8 μm, surpassing the limit traditionally known, thus having a high capacity of reflectivity in contact with the heat of the human body, acting on the blood microcirculation, making the human metabolism to react to the rays being emitted, thus making it possible to attain the auto-regulation of said microcirculation, irrespective of being low or high (circulation), thus reducing the disorders of bad blood microcirculation in a proven way.

DESCRIPTION OF THE DRAWINGS

To complement the present description in order to get a better understanding of the characteristics of the present invention and in accordance with a preferred embodiment thereof, the description is accompanied by a set of attached drawings, wherein, in an exemplified but not limiting the technical field now disclosed the following is illustrated:

in FIG. 4, corresponding to an average increase of 0.82° C. with the use of the fabric containing bioceramic microparticles with high capacity of infrared irradiation. The symbol "x" corresponds to the point of lower cutaneous perfusion and "+" is the point of higher perfusion inside the circle. It is interesting to notice that the point of lower perfusion (x) changed its location when comparing the two images, confirming the microcirculatory change in the region the fabric is used.

DESCRIPTION DETAILED OF THE INVENTION

Figure 1:
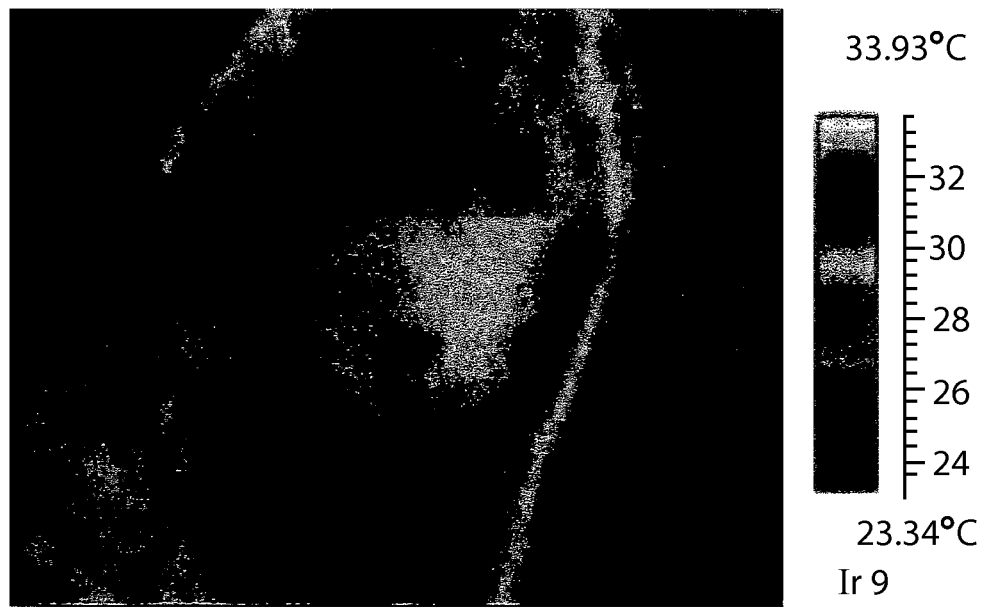
FIG. 1 presents a disc-shaped hypo-radiant area surrounded by several hot spots. The hypo-radiant area corresponds to an area of less cutaneous irrigation. The hot spots correspond to the piercing vases (arteries/veins) that irrigate the skin.
Figure 2:
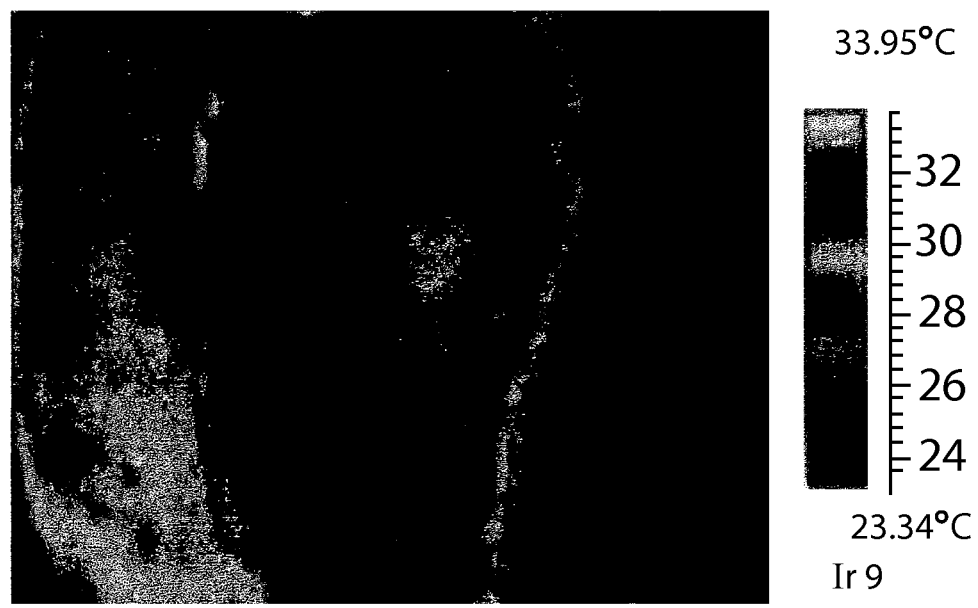
FIG. 2 presents the result one hour after the bioceramic fabric has been used, that is, the fabric containing bioceramic microparticles imbedded into the fibers thereof with high capacity of irradiation in the infrared region, having the characteristics disclosed herein, and it should be noted that the size of the hypo-radiant area has been reduced due to the increase of the diameter of hot spots. The final aspect is of an image—FIG. 1—in a hypo-radiant ring with a small hypo-radiant central area. In the second image—FIG. 2, there was an increase of the cutaneous irrigation due to opening (shunts) of the trenches communicating the piercing vases among one another and increasing the cutaneous circulation as a whole.
Figure 3:
FIGS. 3 and 4 depict the average temperature of the hypo-radiant area of FIG. 3, identified by the circle that it, 28.97° C., and 29.79° C.
Figure 4:

In accordance with the relevant drawings, the present invention is related, to IMPROVEMENTS APPLIED TO A TEXTILE PRODUCT, particularly a textile product containing bioceramic microparticles imbedded into the fibers thereof with high capacity of irradiation in the infrared region, provided to be used in human beings and animals, and more particularly the invention is directed to a textile product containing bioceramic microparticles with high capacity of infrared irradiation which, in contact with the heat of the human body, is capable of transmitting infrared radiation in the range of 3 μm to 14.8 μm=microns, preferentially in the range of 14.8 pm, whose infrared radiation at this wavelength is capable to regulate the blood microcirculation, as a result of its high protection against infrared radiation, the microcirculation being the nervous center of human and/or animal metabolism.

In laboratory assays carried out by both IPT—Institute of Technological Research and Cetiqt—Textile and Chemical Industry Technology Center—an institution affiliated with Senai, said fabric and the method used for evaluating the infrared radiation emission ability of the bioceramic microparticles contained in the textile product—fabric were analyzed, and it was established that it is within the range of 3 μl'll to 14.8 Am (microns), preferentially in the range of 14.8 gm, in order to determine its emissivity and measure its total radiance in said spectral range, thus attaining the results on its reflectance and transmittance. For such, a combination of both measures allows one to evaluate the difference in the capacity of infrared emission between one fabric impregnated containing bioceramic microparticles in its fibers, washed or not, and a fabric without such impregnation and/or properties. Such reflectance and transmittance measurements are carried out with two infrared spectrophotometers through Fourier transform (FTIR). On the other hand, the infrared radiation emission capacity, for the proposal and approval of this patent, was evaluated assuming the occurrence of the emissive effect and the maintenance of the emitting property of the fabric, and when the emissive effect of the fabric containing bioceramic microparticles was of the order of mesh 1,350 it its emissivity at 25° C. (room temperature) was determined and at 37° C. (body average temperature). The temperature of the fabric was maintained around the body temperature by means of heat contact with a resistive heater developed to be used in 'a FTIR spectrophotometer designed to measure the reflectance.

To evaluate the maintenance of the emissive property as the fabric is being washed, the emissivity of fabric samples containing bioceramic microparticles imbedded into the fibers thereof with high capacity of irradiation in the infrared region was determined, which samples have been previously submitted to cycles of 20 washes, 40 washes and 50 to 104 washes. The washing and drying of the fabrics was carried out by the Textiles and Fabrics Laboratory of the IPT—LTC—IPT and by Cetiqt that is duly approved by Inmetro, by adopting washes classified as light according to procedures and the methodology established in ISO—2000 6330 Rule—Textiles—Domestic washing and drying procedures for textile testing, among others.

The total infrared radiance measurement was carried out with a broad band radiometer capable of detecting radiations emitted in the spectral range investigated, resulting in a radiation of the order of 14.8 μm wherein the fabric was kept at 37° C. through heat contact with a prism provided with a thermostat.

For the determination of the emissivity, the spectral reflectance measurements was carried out at room temperature)(25+/−1° C. and close to the body temperature of (37+/−1)° C., while the spectral transmittance measurements was carried out only at room temperature (25+/−1)° C. In all the measurements of emissivity and total radiance the fabric was gently stretched to remain smooth and unwrinkled without causing the same to be fully stretched.

The infrared spectral reflectance measurement of fabrics was carried out by using a Nicolet spectrophotometer, Avatar model, at a temperature of (37+/−1)° C. attained with a resistive heater connected to a flat brass plate contacting the fabric directly. The stability of the temperature of the fabric was attained by feeding the resistive heater with a stabilized current and voltage source. Moreover, the fabric temperature gradient between the end of the plate and the measurement point was monitored with a thermocouple. The infrared spectral transmittance measurement of fabrics was carried out by using a Nicolet spectrophotometer at room temperature, (25+/−1)° C.

The total infrared radiance measurement of fabrics was carried out with an electrically calibrated pyro-electric radiometer (ECPR) using a broad band pyro-electric detector capable of detecting radiations emitted between the ultraviolet range (200 pm) and the intermediate infrared range (22,000 μm), the fabric being kept at (37+/−1)° C., by means of thermal contact with the flat face of a prism provided with a thermostat, whose temperature is kept by circulating the water of a stabilized thermal bath. Also, the temperature of the fabric measurement area was monitored with a thermocouple.

The total infrared radiance measurement at room temperature, (25+/−1)° C. was also monitored with a thermocouple and the stability of the ambient conditioning of the laboratory allowed for a low variation of (25+1−1)° C. in the measurement area. The thermal bath of the fabric for the application of the bioceramic microparticles with high capacity of irradiation in the infrared region takes place along its whole extension, thus the total infrared radiance is spatially uniform and the fabric can be considered a Lambert source and, therefore, the infrared radiance (L), can be attained through the irradiance (Eivband) that reaches the photodetector inside the solid angle (0) defined by the circular area of the sample (a) and by the photodetector-sample distance (d):

L=Eivband/Ω=Eivband d²/A

The graphs given hereinbelow show the results of the reflectance and transmittance of both the bioceramic material/fabric and the fabrics not containing bioceramic microparticles, particularly in the disclosed range of 14.8 microns. The table below lists the codes used in the identification of assayed fabrics, for the purpose of identifying the applied terminology, viz:

| Code | Meaning |
| --- | --- |
| μm | Micron |
| SC | Fabric without ceramic |
| CC | Fabric with ceramic |
| SL | Unwashed fabric |
| 20L | Fabric washed 20 times |
| 40L | Fabric washed 40 times |
| 50L+ | Fabric washed 50 times or more - up to 104 times |
| 25 | Fabric at room temperature |
| 37 | Fabric at a temperature of 37 degrees, the human body average temperature |

Figure 5:
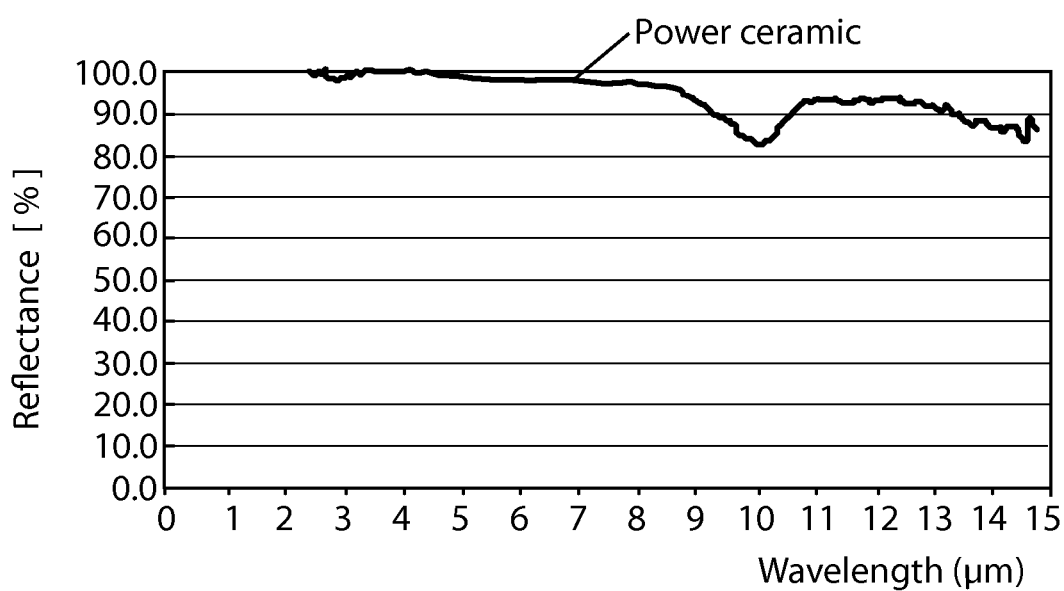
FIG. 5 depicts a graph where the result of the reflectance of the pure bioceramic powder at room temperature indicating a high reflectivity in the whole infrared range is shown.

Through the graph of FIG. 5, it can be seen that the result of the reflectance of the pure bioceramic powder at room temperature shows a high reflectivity in the whole infrared range, always above 82%, with a small characteristic attenuation in the range between 7.5 urn and 11.1 Rm. Thus, it can be understood that the impregnation of bioceramic microparticles in fibers of the fabric tends to transfer a high reflectivity to the composed material and, therefore, lower its infrared emissivity in a more accentuated form outside the band and less accentuated inside the characteristic range.

Figure 6:
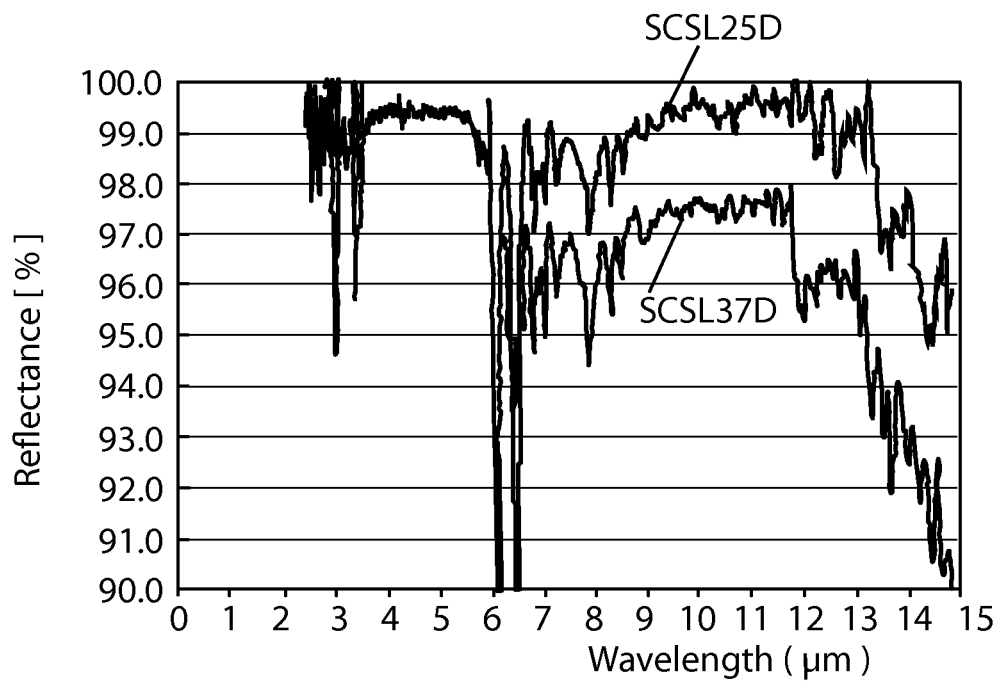
FIGS. 6 and 7 represent, respectively, graphs that illustrate the reflectance of the non-washed fabric without bioceramic microparticles and the reflectance of the un-washed heated fabric containing bioceramic microparticles.
Figure 7:
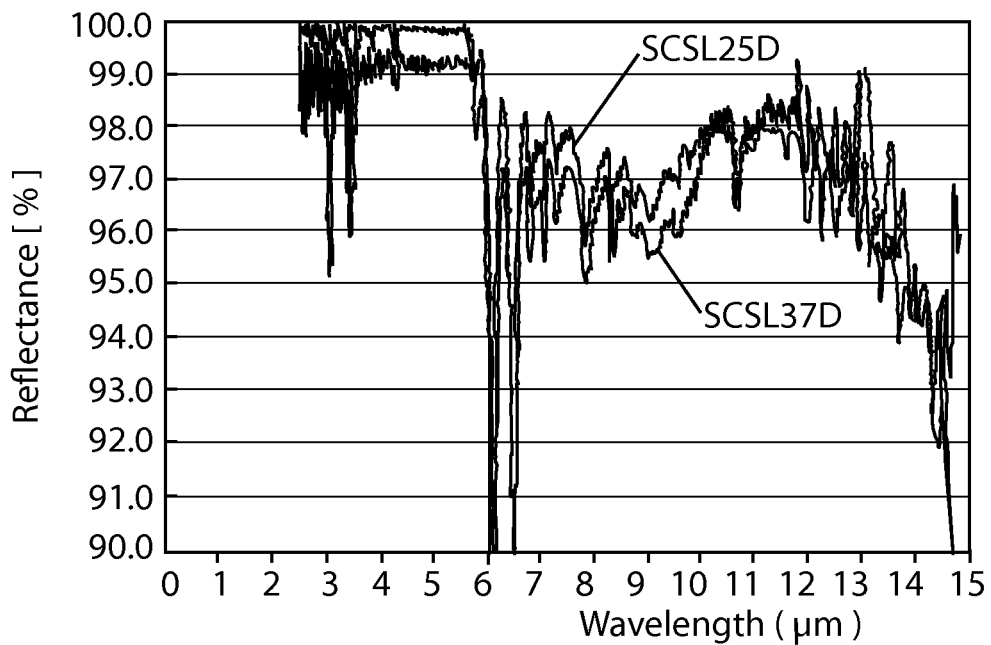

In the graphs of FIGS. 6 and 7, it can be seen that the reflectance of the unwashed fabric without bioceramic microparticles at the room temperature, 25° C., and at the human body temperature of 37° C., on any of its sides, right or reverse, is shown with a clear attenuation in the whole infrared range of the heated fabric particularly compared with the fabric at room temperature, what can be reflected into an increase of the total emissivity of the fabric at the temperature of 37° C. On the other hand, the reflectance of the heated unwashed fabric containing bioceramic microparticles at room temperature, 25° C., and at the human body temperature of 37° C., on any of its sides, is increased almost in the whole infrared range, compared to the same fabric at room temperature. By comparing the bioceramic fabric to the fabric without bioceramic, both of them washed and on both sides, at the human body temperature of 37° C. there is an increase of the reflectance in the whole infrared range spectrum (with the exception of a small range between 8.7

μm and 9.7 μm inside the characteristic range of the bioceramic powder), while at room temperature there is a reduction in the reflectance in almost the whole infrared range, an the result is that the total emissivity of, the fabric containing bioceramic, compared to the fabric without bioceramic, is reduced at the temperature of 37° C. and approximately 1.7 times higher at room temperature.

Thus, with regard to the reflectance of the unwashed fabric containing bioceramic at room temperature, 25° C. and at the human body temperature of 37° C., on any of its sides, it is clear that the reflectance of the heated fabric in the whole infrared range is higher, compared to the same fabric at room temperature (25° C.), thus characterizing a superior reflective behavior than the one of the fabric without bioceramic.

Figure 8:
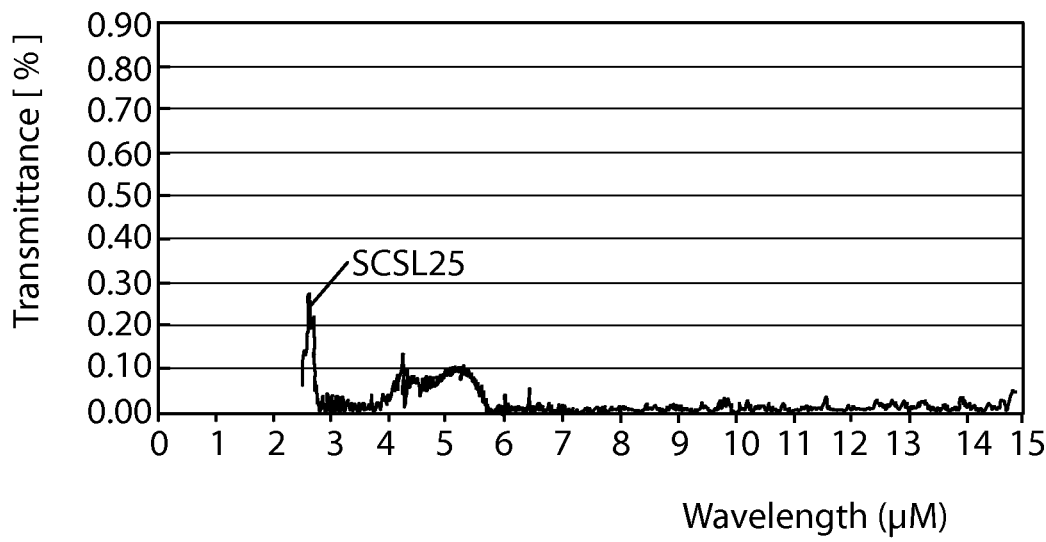
FIG. 8 depicts a graph showing an increase in the transmittance in the whole infrared range, with an average value around 0.7% against 0.05% of the one lacking bioceramic microparticles.
Figure 9:
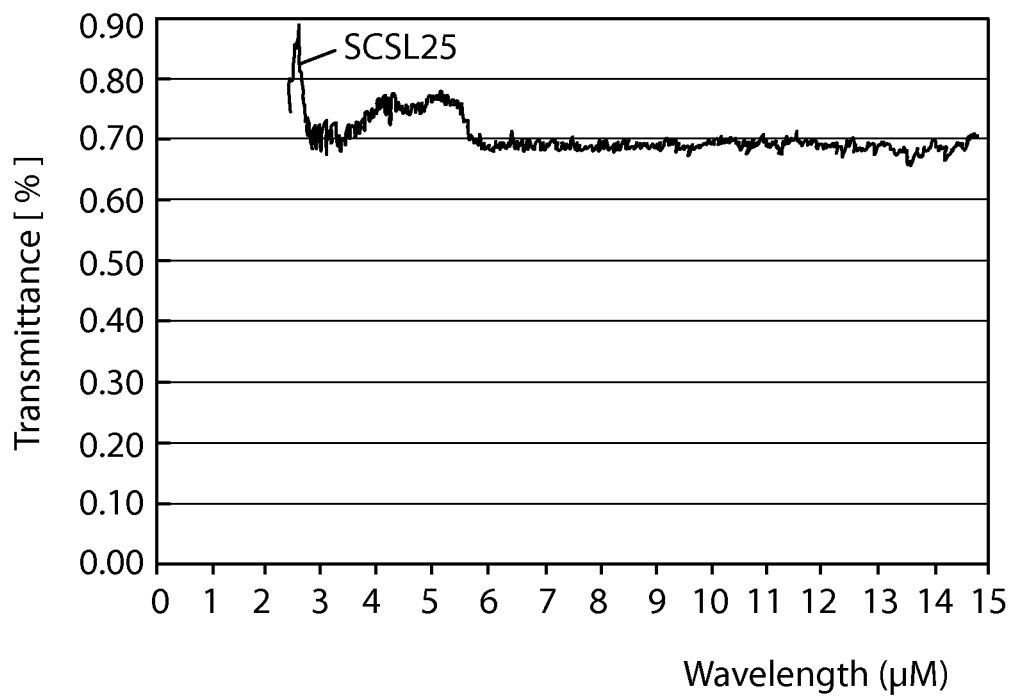
FIG. 9 represents a graph illustrating that the fabric, in a non-striated form, transmits very poorly in the whole infrared range, always presenting spectral transmittances lower than 0.9%.

As to the transmittance, in relation to the unwashed fabric containing bioceramic at room temperature, the graph of FIG. 9 was attained due to the fact that said fabric, in a non-striated form, transmits very poorly in the whole infrared range, showing spectral transmittances always lower than 0.9%. Compared to the fabric without bioceramic microparticles in the graph of FIG. 8, it can be noticed that there is an increase in the transmittance in the infrared range, with an average value around 0.7% against 0.05% of the fabric without bioceramic microparticles. The conclusion is that the fabric being analyzed that contains bioceramic microparticles imbedded into the fibers thereof, with an infrared radiation transmittance in the 14.8 micron range, increases the transmittance in the whole infrared range and, therefore, always reduces the emissivity.

Compared to the reflectance, the transmittance and the emissivity of the unwashed fabric containing bioceramic microparticles at room temperature, 25° C., and at the human body temperature of 37° C., we have:

| Fabric | Refletance | Transmittance | Emissivity Outside the band/ inside the band/Total |
|---|---|---|---|
| CCSL25D | 97.185 | 0.699 | 0.019/0.025/0.21 |
| CCSL37D | 97.396 | 0.699 | 0.019/0.020/0.019 |
| CCSL25A | 97.506 | 0.699 | 0.018/0.018/0.018 |
| CCSL37A | 97.285 | 0.699 | 0.020/0.021/0.020 |

In accordance with the comparison for attaining the reflectance results between fabrics containing bioceramic microparticles, not washed and washed, at room temperature, the conclusion is that even after 50 washes=up to 104 washes, the spectral reflectance that differentiates the fabric containing bioceramic microparticles from the fabric without bioceramic is still maintained, thus allowing the washed samples to keep a higher emissivity than that of the fabric without bioceramic microparticles at room temperature.

In the case of the reflectance, the unwashed fabrics containing bioceramic microparticles show a high reflectivity compared to that of the fabrics without bioceramic, and those washed up to 104 times show a higher reflectivity than the fabrics without bioceramic, at the human body temperature of 37° C.

The transmittance of the washed fabrics containing bioceramic microparticles at room temperature, in a non-striated form, shows that they transmit very poorly in the whole infrared range, with spectral transmittances below 0.28% so that, compared to the fabric without bioceramic microparticles, it can be noticed that a low transmittance of up to 104 washes is maintained even to a small extent.

In comparison to the reflectance, the transmittance and the emissivity of the washed fabric containing bioceramic at room temperature, 25/C and at the human body temperature of 37° C., we have:

| Fabric | Reflectance | Transmittance | Emissivity Outside the band/ Inside the band/Total |
|---|---|---|---|
| CC20L25D | 98.265 | 0.015 | 0.017/0.019/0.017 |
| CC20L37D | 97.362 | 0.015 | 0.026/0.027/0.026 |
| CC4OL25D | 97.448 | 0.012 | 0.025/0.026/0.025 |
| CC4OL37D | 97.545 | 0.012 | 0.026/0.022/0.024 |
| CC50L25D | 97.766 | 0.012 | 0.023/0.020/0.022 |
| CC5OL37D | 97.185. | 0.012 | 0.029/0.025/0.028 |

The infrared total radiance and the emissivity of the fabrics containing bioceramic microparticles, at the human body temperature of 37° C., on any of the sides, are presented in the ranges indicated hereinbelow, so that possibilities of lower or higher variations of the order of 30% can be foreseen, therefore attaining practically equal results on both sides, since the fabric is uniformly bathed in a colorful liquid containing the bioceramic microparticles in a range between 2% and 15%, preferentially of 7%.

| Fabric | Radiance of fabric at 37° C. [mW/cm² sr] | |
|---|---|---|
| | Side A | Side B |
| SCSL | 1.445 | 1.458 |
| CCSL | 1.353 | 1.436 |
| CC2OL | 1.415 | 1.468 |
| CC4OL | 1.410 | 1.415 |
| CC5OL | 1.413 | 1.494 |

The results of radiance on any side show that the infrared radiation emitted by fabrics without bioceramic microparticles or containing bioceramic microparticles, washed or not washed, is similar, even though the fabrics containing bioceramic microparticles imbedded into the fibers thereof always emit a little less than those without bioceramic microparticles. This result is consistent with the result attained by emissivity reduction spectrophotometry in fabrics containing bioceramic microparticles (washed or not washed), compared to the fabric without bioceramic microparticles. The results of radiance on the reverse side are similar.

The black body radiance at the human body temperature of 37° C., in the infrared range between 0.78 and 22.0 [mW/cm² sr] is allocated in the order of 13.29%. By comparing the radiance of the bioceramic-containing fabric to the radiance of the black body, the emissivity of the bioceramic-containing fabric at the human body temperature of 37° C. was determined in the infrared range between 0.78 and 22.0 jam, as per the table below:

| Fabric | Radiance of fabric at 37° C. [mW/cm² sr] | |
|---|---|---|
| | Side A | Side B |
| SCSL | 0.109 | 0.110 |
| CCSL | 0.102 | 0.108 |
| CC2OL | 0.106 | 0.110 |
| CC4OL | 0.106 | 0.106 |
| CC5OL | 0.106 | 0.112 |

The infrared range measured with the pyro-electric radiometer in the range between 0.78 and 22.0 µm, is higher that the range measured with FTIR spectrophotometers (3.0 to 14.8 µn), consisting of different fabric emissivity results, of the order of 11% with radiometry and 3.5% with spectrophotometry, despite the fact that the emissivities have the same order of magnitude.

The powder in the form of bioceramic microparticles that are impregnated into the fabric by means of a uniform bath is a highly reflective material in the infrared range that shows reflectances close to 100% between 2.8 µm and 8.2 µm, above 82% inside the characteristic range between 8.2 µm and 11.1 µm and a 90% average between 11.1 µm and 14.8 µm. For each $m^2$ (square meter) of fabric to attain the high capacity of infrared reflectivity applied herein, it is necessary to apply from 2% to 15% bioceramic microparticles, preferentially 7%, which is dissolved and diluted in a dye, and the respective fabric is immersed into the dye, thus being submitted to a uniform bath on both sides.

The respective bioceramic microparticle is provided with aluminum silicate, zinc oxide, barium magnesium carbonate, and may be added to other components of less importance, but its consistency must be based on the microparticles, that is, with a quality of microparts to enable the fusion/fixation to the fabric with a quality that may assure same to remain in said fabric even up to 104 washes in view of its unique imprecise impregnation. This microproperty also makes it possible to disperse in the dye, be absorbed by the fabric, and mainly reflected when in contact with the heat/human body temperature. The dye is only an application vehicle that is not provided with any particular characteristic, that is, it is traditionally used.

The unwashed fabric without bioceramic microparticles shows a low reflectivity in the infrared range on both sides, right and reverse, in relation to the washed or unwashed bioceramic-containing fabric. On the other hand, the fabric containing bioceramic microparticles shows a very low infrared spectral transmission, of a maximum value of 0.27% and in general very close to zero, and said characteristics (reflection and transmission) indicate that the emissive behavior of the fabric is basically regulated by the reflective behavior, that is, the reflectivity is critical to the emissive behavior of the fabric. Moreover, the reflective characteristic combined with the low emissivity characterizes the fabric as a material of high protection against the infrared radiation.

When the fabric containing bioceramic microparticles is warmed to 37° C.—the human body temperature ¬ the infrared reflectivity on any of the sides of the fabric increases, thus showing a behavior contrary to the one of the fabric without bioceramic, what can be explained by the high reflectivity of the bioceramic microparticle incorporated thereto, so that in the fabric containing bioceramic microparticles the emissivity at 37° C. is lower than that in the fabric without bioceramic and higher than that at room temperature. That is, at the temperature of 37° C. the fabric containing bioceramic microparticles presents a higher protection against the infrared radiation.

At room temperature, 25° C., the unwashed fabric containing bioceramic microparticles does not present a lower total reflectivity, as well as in practically the whole infrared range in relation to the fabric in contact with the human body at an average temperature of 37° C. As the fabric is washed, it tends to have the former reflectivity and be similar to the fabric without bioceramic microparticles (not washed), however, such characteristics are recognized in the fabric only after it is washed 104 times.

When heated to 37° C., the fabrics containing bioceramic microparticles, not washed or washed, present a higher reflectivity than that without bioceramic microparticles.

The fabric without bioceramic microparticles presents a reflectivity whose characteristic is a low emissivity ($\epsilon$=0.013; T=25° C.), although it increases as the temperature rises ($\epsilon$=−0.035; T=37° C.); a behavior observed on both sides.

The fabric containing bioceramic microparticles, as the resulted of two materials of low emissivity, also presents a low emissivity ($\epsilon$<0.022).

The respective unwashed fabric containing bioceramic microparticles, in relation to the fabric without bioceramic, shows that it can reduce the emissivity and increase the infrared reflectivity, thus showing a totally contrary behavior.

While the reflectance of the fabric containing bioceramic microparticles increases when the fabric is heated, that is, when it goes from the room temperature and reaches the average human body temperature, thus concluding that the reflectance of the fabric containing bioceramic microparticles is higher and its emissivity is lower.

In the course of the measurement of the normal total emissivity of the bioceramic-containing fabric, in the infrared range between 3.0 µm and 14.8 µm, preferentially in the range of 14.8 µm, either at the room temperature, 25° C. or at the human body temperature of 37/C, washed or not washed, the results indicate that it shows a low emissivity lower than 0.03%, associated to a total high reflectivity higher than 97%, thus characterizing the fabric containing bioceramic microparticles as a material of high protection against the infrared radiation that makes it possible to self-regulate the microcirculation. The emission of infrared radiation by the fabric containing bioceramic microparticles at 37° C., in the infrared range from 0.78 µm to 22.0 µm is of about 1.4 mW/$cm^2$ sr, representing an average emissivity of 0.11 in this spectrum range.

The application of bioceramic microparticles to the fabric allows same to develop, on any of its sides, a reflective/emissive behavior contrary to that occurring in the fabric without bioceramic, when it is heated. Indeed, when the fabric is heated from the room temperature (25° C.) to the average human body temperature (37° C.) on any of the sides of the fabric containing microparticles bioceramic it can increase the infrared reflectivity (from 97.18 to 97.40) and reduce the emissivity from 0.021 to 0.019 in the infrared range of 14.8 µm.

The application of the bioceramic in the form of microparticles to a material having a very high infrared reflectivity reduces the emissivity of the fabric thus composed, when it is heated close to the average human body temperature (37° C.), thus compensating for the natural increase of the emissivity of the fabric (without bioceramic) itself through heating. Thus, the bioceramic-containing fabric increases the protection against the infrared radiation as it is heated to the average human body temperature and releases this protection as it is cooled to the room temperature, becoming a little more emissive in this situation. Then, when it changes from the room temperature to the average human body temperature, the fabric containing bioceramic microparticles acts like a mechanism between two behaviors (lower protection/higher infrared emissivity) to (higher protection/lower infrared emissivity). It is important to stress the fact that although the contrary is very interesting, the emissivity changes that occurred do not vary significantly, being kept below 0.03%.

As to the maintenance of the emissive characteristics, in the infrared range between 3.0 μm and '14.8 μm, preferentially in the range of 14.8 μm, it was noticed that as the fabric is washed, only after 104 times it tends to recover the reflectivity of the fabric without bioceramic, and also that the efficiency of the inverse mechanism of infrared protection/emission under heating at 37° C. is reduced, although a better performance of infrared protection/irradiation/reflectivity than in the fabric without application of bioceramic microparticles may be noticed in all the washed fabrics.

A group composed of 20 volunteers with a moderate degree of cellulite was submitted to a treatment with the occlusion of the fabric containing bioceramic in one of the thighs, and the other whose applied fabric was not submitted to any washing treatment. An anti-cellulite cream was applied to the other thigh, at the affected sites, usually at night. After a period of 4 (four) weeks, the examining dermatologists detected an average improvement of 65% in the thighs of the group of people treated with the fabric with bioceramic microparticles impregnated thereto, with a high capacity of reflectivity.

In a second research, 24 people with ages between 20 and 45 years that presented the characteristics of normal skin, phototypes II and III according to the Fitzpatrick scale and gynoid lipodystrophy in stage II according to the Numgerger-Muller scale were selected from a database. The volunteers were instructed to suspend the use of any cosmetics applied to the test sites. (gluteus and thighs) for 48 hours before the beginning of test, said group being divided into 3 groups of study, each containing eight participants: Lymphatic draining (D), Cosmetic Treatment (c) and Treatment with the bioceramic-containing fabric I (B). The equipment used were a thermographic camera Varioscan Compact 3012 Jenoptik, Kodak digital camera Dx 6490, Thermographic analysis software ThermoView 1,0, Photographic image analysis Scion image for windows, static analysis grandpad prism 4.03. The purpose of this study, by means of objective techniques, is the efficacy of the anti-cellulite treatment associated with the use of the bioceramic-containing fabric I emitting infrared radiation between 3.0 m and 14.8 μm, preferentially at 14.8 μm, through the manual lymphatic draining technique and the use of a cosmetic anti-cellulite cream, considering periods of treatments of 30 days.

From the objective evaluation of the computerized thermography, it was observed that all the treatments generated significant improvements in the local blood microcirculation, and also the fabric I containing bioceramic microparticles irradiating a high infrared content, inferring in the reduction of fluid and metabolites, thus improving the aspect of the skin, in view of the high infrared reflectance.

It was evidenced that the fabric I containing bioceramic microparticles irradiating infrared in the 14.8 range microns is capable of causing the reaction of the blood microcirculation in a few hours, providing its regulation and stabilization. Said fabric, with its properties and characteristics described, caused a cutaneous irrigation, thus regulating the blood microcirculation.

One edema, that is the accumulation of liquids and may appear as the manifestation of heart, liver and kidney diseases, slight malnutrition, hypotyroidism and more usually blockage of the veins, venous and lymphatic vases insufficiency, in the case of varix, for example, is presented in the form of lymphedema. On the other hand, the lymphedema diminishes the speed of the blood microcirculation and impairs the nutrition and the efficiency of tissues.

The application of the fabric I containing bioceramic microparticles emitting infrared radiation results in the activation and automatically in the regulation of the microcirculation, thus activating the metabolism, since, as recited hereinabove, the application of said bioceramic containing infrared radiation, when getting in contact with the heat of the human body, allows for a reflective/emissive behavior, as previously demonstrated, in the proportions and intervals of room temperature×average human body temperature, causing an increase in the infrared reflectivity. Therefore, there is a thermal redistribution in the lower limbs when said fabric is exposed to the respective limbs and in contact with the heat of the human body.

The present invention that is related to the textile product containing bioceramic microparticles incorporated thereto emitting infrared radiation provided to be used in human beings and animals, more particularly said textile product containing bioceramic microparticles emitting infrared radiation that, in contact with the heat of the human body, is capable of emitting infrared radiation in the range from 3.0 μm to 14.8 μm preferentially of 14.8 μm, that in this length/range/band is capable of regulating and stabilizing the microcirculation, is not limited to the application thereof and the details and steps described herein, and other embodiments also are possible provided that they are restricted to the principles and parameters shown and disclosed as novelty herein, being understood that the purpose of the terminology applied herein is to describe and not limit the scope of the invention.

What is claimed is:

1. A textile having fibers containing bioceramic powder integrally incorporated into the fibers, wherein the bioceramic powder incorporated into the textile has a reflectance of substantially close to 100% in a wavelength between 2.8 μm and 8.2 μm, at least 82% within the range between 8.2 μm and 11.1 μm and a reflectance of substantially 90% between 11.1 μm and 14.8 μm, when the bioceramic powder is in contact with heat of a body, in a wavelength regulating the blood microcirculation of a body; according to a self-shielding in the transmittance of the infrared radiation throughout the physical body that is in contact with the textile.

2. The textile according to claim 1, wherein the infrared radiation is in the wavelength of 14.8 μm.

3. The textile according to claim 1, wherein the textile is highly shielded to infrared radiation, due to an inherent self-shielding ability enabling the regulation of the blood microcirculation of the body.

4. The textile according to claim 1, wherein the reflectance of the bioceramic powder applied to the textile has a reflectivity of at least 82% at a temperature of 25° C. at an infrared range between 7.5 gm and 11.1 μm.

5. The textile according to claim 1, wherein the reflectance of the textile with the bioceramic powder incorporated and unwashed increases in substantially the entire infrared range, at all sides, from a room temperature of 25° C. to a body temperature of 37° C.; to a maximum of 1.7 times.

6. The textile according to claim 1, wherein a right side of an unwashed textile containing bioceramic powder at a room temperature of 25° C. has a reflectance of 97.185, a transmittance of 0.699 and emissivity in a ratio outside the band/inside the band of 0.019/0.025 with a total of 0.021, and wherein a right side of an unwashed textile containing bioceramic powder at a body temperature of 37° C. has a reflectance of 97.396, a transmittance of 0.699 and emissivity in a ratio outside the band/inside the band of 0.019/0.020 with a total of 0.019, and wherein a reverse side of an unwashed textile containing bioceramic powder at a room temperature of 25° C. has a reflectance of 97.506, a transmittance of 0.699 and emissivity in a ratio outside the band/inside the band of 0.018/0.018 with a total of 0.018, and wherein a reverse side of an unwashed textile containing bioceramic powder at a body temperature of 37° C. has a reflectance of 97.285, a transmittance of 0.699 and emissivity in a ratio outside the band/inside the band of 0.020/0.021 with a total of 0.020.

7. The textile according to claim 1, wherein a right side of a washed textile for 20 times containing bioceramic powder at a room temperature of 25° C. has a reflectance of 98.265, a transmittance of 0.015 and emissivity in a ratio outside the band/inside the band of 0.017/0.019 with a total of 0.017, and wherein a right side of a washed textile, for 20 times containing bioceramic powder at a body temperature of 37° C. has a reflectance of 97.362, a transmittance of 0.015 and emissivity in a ratio outside the band/inside the band of 0.026/0.027 with a total of 0.026, and wherein a right side of a washed textile for 40 times containing bioceramic powder at a room temperature of 25° C. has a reflectance of 97.448, a transmittance of 0.012 and emissivity in a ratio outside the band/inside the band of 0.025/0.026 with a total of 0.025, and wherein a right side of a washed textile for 40 times containing bioceramic powder at a body temperature of 37° C. has a reflectance of 97.545, a transmittance of 0.012 and emissivity in a ratio outside the band/inside the band of 0.026/0.022 with a total of 0.024, and wherein a right side of a washed textile for 50 times containing bioceramic powder at a room temperature of 25° C. has a reflectance of 97.766, a transmittance of 0.012 and emissivity in a ratio outside the band/inside the band of 0.023/0.020 with a total of 0.022, and wherein a right side of a washed textile for 50 times containing bioceramic powder at a body temperature of 37° C. has a reflectance of 97.185, a transmittance of 0.012 and emissivity in a ratio outside the band/inside the band of 0.029/0.025 with a total of 0.028.

8. The textile according to claim 1, wherein a right side of an unwashed textile without bioceramic powder has a radiance of 1,445 at a body temperature of 37° C. and a reverse side of an unwashed textile without bioceramic powder has a radiance of 1,458 at a body temperature of 37° C., and wherein a right side of the unwashed textile containing bioceramic powder has a radiance of 1,353 at a body temperature of 37° C.: and a reverse side of an unwashed textile containing bioceramic powder has a radiance of 1,436 at a body temperature of 37° C., and wherein a right side of a washed textile for 20 times containing bioceramic powder has a radiance of 1,415 at a body temperature of 37° C. and a reverse side of a washed textile for 20 times textile containing bioceramic powder has a radiance of 1,468 at a body temperature of 37° C., and wherein a right side of a washed textile for 40 times containing bioceramic powder has a radiance of 1,410 at a body temperature of 37° C. and a reverse side of a washed textile for 20 times textile containing bioceramic powder has a radiance of 1,415 at a body temperature of 37° C., and wherein a right side of a washed textile for 50 times containing bioceramic powder has a radiance of 1,413 at a body temperature of 37° C. and a reverse side of a washed textile for 20 times textile containing bioceramic powder has a radiance of 1,494 at a body temperature of 37° C.

9. The textile according to claim 1, wherein the bioceramic powder is microparticles.

10. The textile according to claim 1, having an infrared spectral transmission of a maximum of 0.27%.

11. The textile according to claim 1, wherein when the bioceramic powder is in contact with heat of a body at a temperature of 37° C., the infrared reflectivity of all sides of the textile increases.

12. The textile according to claim 1, wherein when the bioceramic powder is in contact with heat of a body at a temperature of 37° C., the infrared reflectivity of all sides of a washed or an unwashed textile increases.

13. The textile according to claim 1, wherein when the bioceramic powder is in contact with heat of a body at a temperature of 37° C., the infrared reflectivity of all sides of a washed textile increases up to a maximum of 104 washings.

14. The textile according to claim 1, having total regular emissivity lower than 0.03%, directly associated with a total high reflectivity higher than 97% in the infrared range between 3.0 µm and 14.8 µm, at a room temperature of 25° C. or at a body temperature of 37° C., when washed or unwashed; and an emissivity of about 1.4 mW/cm$^2$ sr in the infrared range between 0.78 µm to 22.0 µm, representing an average emissivity of 0.11 in the spectrum range.

15. The textile according to claim 1, wherein the body is a human body or an animal body.

16. The textile according to claim 1, wherein the textile is a material of very high infrared reflectivity, with the emissivity reduction, when heated due to the textile is placed in contact with the human body at a temperature of 37° C., thus increasing the shielding to infrared radiation to the extent that the textile is heated in the average human body temperature at 37° C.

17. The textile according to claim 1, wherein the textile is part of a therapeutic product constructed and arranged to assist in the activation and automatically assist in the blood microcirculation regulation activating the metabolism, producing increased infrared reflectivity, allowing the thermal redistribution of the lower limbs, when the textile is placed in contact with the human or animal body.

* * * * *